United States Patent
Hwang et al.

(10) Patent No.: US 11,090,418 B2
(45) Date of Patent: Aug. 17, 2021

(54) BREAST PUMP

(71) Applicant: Hyo Soon Hwang, Gyeonggi-do (KR)

(72) Inventors: Hyo Soon Hwang, Gyeonggi-do (KR); Jung Hee Kim, Gyeonggi-do (KR)

(73) Assignee: Hyo Soon Hwang

( * ) Notice: Subject to any disclaimer, the term of this patent is extended or adjusted under 35 U.S.C. 154(b) by 0 days.

(21) Appl. No.: 16/962,507

(22) PCT Filed: Feb. 21, 2019

(86) PCT No.: PCT/KR2019/002145
§ 371 (c)(1),
(2) Date: Jul. 15, 2020

(87) PCT Pub. No.: WO2019/194418
PCT Pub. Date: Oct. 10, 2019

(65) Prior Publication Data
US 2021/0093761 A1   Apr. 1, 2021

(30) Foreign Application Priority Data
Apr. 5, 2018 (KR) .................. 10-2018-0039783

(51) Int. Cl.
*A61M 1/06* (2006.01)
*A61M 39/10* (2006.01)
*A61M 39/22* (2006.01)

(52) U.S. Cl.
CPC ............ *A61M 1/066* (2014.02); *A61M 39/10* (2013.01); *A61M 39/22* (2013.01)

(58) Field of Classification Search
CPC ........ A61M 1/06; A61M 1/062; A61M 1/064; A61M 1/066
See application file for complete search history.

(56) References Cited

U.S. PATENT DOCUMENTS

2014/0052056 A1   2/2014   Garbez et al.
2018/0008758 A1*  1/2018   Garbez .............. A61M 1/0037

FOREIGN PATENT DOCUMENTS

KR   20-2012-0003945   6/2012
KR   20-2013-0000616   1/2013
(Continued)

OTHER PUBLICATIONS

International Search Report dated Jun. 11, 2019 in corresponding South Korean Patent Application No. PCT/KR2019/002145 [with English machine translation].
(Continued)

*Primary Examiner* — Nathan R Price
*Assistant Examiner* — Melissa A Snyder
(74) *Attorney, Agent, or Firm* — Grossman, Tucker, Perreault & Pfleger, PLLC (57) ABSTRACT

A breast pump is disclosed. According to an aspect of the present invention, there is provided a breast pump comprising a contact housing comprising a protruding part configured to correspond to a mother's nipple and extend toward the front and a breast milk outlet hole formed at the protruding part; a cap connector coupled to cover an end of the protruding part to form a first inner space between the end of the protruding part and itself and comprising a breast milk outlet tube linked with the breast milk outlet hole and the first inner space; a funnel connector on the cap connector to form a second inner space; a storage housing comprising a coupling hole to correspond to the second inner space of the funnel connector and detachably coupled with the contact housing; a lid coupled to cover the second inner space of the funnel connector through the coupling hole of the storage housing; and a flow separation membrane configured to separate the space between the funnel connector and the lid.

7 Claims, 11 Drawing Sheets

(56) References Cited

FOREIGN PATENT DOCUMENTS

| KR | 10-1463088 | 11/2014 | | |
|----|------------|---------|---|---|
| KR | 10-1622768 | 5/2016 | | |
| KR | 101622768 B1 | * | 5/2016 | ............ A61M 1/064 |

OTHER PUBLICATIONS

Office Action dated Aug. 26, 2019 in corresponding South Korean Patent Application No. 10-2018-0039783 [with English machine translation].
Office Action dated Feb. 13, 2020 in corresponding South Korean Patent Application No. 10-2018-0039783 [with English machine translation].
Malaysian Office Action dated Oct. 15, 2020 in corresponding Malaysian Patent Application Serial No. PI2020003664.
Malaysian Office Action dated Dec. 3, 2020 in corresponding Malaysian Patent Application Serial No. PI2020003664.
Malaysian Office Action dated Feb. 16, 2021 in corresponding Malaysian Patent Application Serial No. PI2020003664.

* cited by examiner

BREAST PUMP

BACKGROUND

1. Field

The present invention relates to a breast pump, and more particularly, to a breast pump that allows a user to use both hands freely during extracting breast milk.

2. Description of Related Art

Various types of breast pumps are commercially available and are classified into manual and electric types depending on the type of power source.

The manual breast pump includes a funnel-shaped inhaler fitting over the breast, a vacuum pump in the form of a rubber ball for generating air pressure in the inhaler, and a bottle to store the breast milk introduced into the inhaler. Such a manual breast pump requires repeated cycles of pressing and releasing the vacuum pump with a woman's one hand while closely holding the inhaler to the breast with the other hand. Here, since the pressure of pumping changes air pressure and thus sufficient air pressure cannot be generated, it is not efficacious and not comfortable.

The electric breast pump includes a pneumatic generating pump having a motor and an air cylinder, a funnel-shaped inhaler connected to the pneumatic generating pump to fit over the breast, and a bottle to store the breast milk introduced into the inhaler. Such an electric breast pump has an advantage in that it is easy to use due to less amount of effort required to use the pump. However, even in this case, since a nursing mother needs to continuously hold the bottle, it causes discomfort during operation.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the present invention provide a breast pump that allows a nursing mother to use both hands freely during operation and provides easy cleaning and easy maintenance.

According to an aspect of the present invention, there is provided a breast pump including a contact housing including a protruding part configured to correspond to a mother's nipple and extend toward the front and a breast milk outlet formed at the protruding part; a cap connector coupled to cover an end of the protruding part to form a first inner space between the end of the protruding part and itself and including a breast milk outlet tube linked with the breast milk outlet and the first inner space; a funnel connector on the cap connector to form a second inner space; a storage housing including a coupling hole to correspond to the second inner space of the funnel connector and detachably coupled with the contact housing; a lid coupled to cover the second inner space of the funnel connector through the coupling hole of the storage housing; and a flow separation membrane configured to separate the space between the funnel connector and the lid.

According to embodiments of the present invention, a breast pump is able to allow a nursing mother freely using both hands while pumping the breast pump and further provide easy cleaning and easy maintenance.

DETAILED DESCRIPTION

The terms used in the description are intended to describe certain embodiments only, and shall by no means restrict the present disclosure. Unless clearly used otherwise, expressions in the singular number include a plural meaning.

In the present description, an expression such as "comprising" or "consisting of" is intended to designate a characteristic, a number, a step, an operation, an element, a part or combinations thereof, and shall not be construed to preclude any presence or possibility of one or more other characteristics, numbers, steps, operations, elements, parts or combinations thereof. In addition, in the present description, an expression such as "upper" or "on" means that it is located above or below a target part, and does not necessarily mean that it is located above the gravity direction.

Further, when one element is described to be "coupled" or "linked" to another element, it does not refer to a physical, direct contact between these elements only, but it shall also include the possibility of yet another element being interposed between these elements and each of these elements being in contact with said yet another element.

The drawings may not be to scale, and the relative size, proportions, and depiction of elements in the drawings may be exaggerated for clarity, illustration, and convenience.

The terms such as "first" and "second" are merely identifiers for distinguishing one element from other identical or corresponding elements, but the above elements shall not be restricted to the above terms.

The breast pump according to certain embodiments of the disclosure will be described below in more detail with reference to the accompanying drawings, in which those components are rendered the same reference number that are the same or are in correspondence, regardless of the figure number, and redundant explanations are omitted.

A breast pump according to an embodiment of the present invention, which is a device for extracting milk by applying a vacuum pressure to a breast of a lactating woman, allows the woman freely using her hands during operation since it can be worn inside a bra, provides easy cleaning and easy maintenances since a linking pathway 310 between a cap connector 200 and a funnel connector 300 is configured to be the shortest distance, and prevents breast milk from flowing backward through a flow path to which the vacuum pressure is applied.

Figure 1:
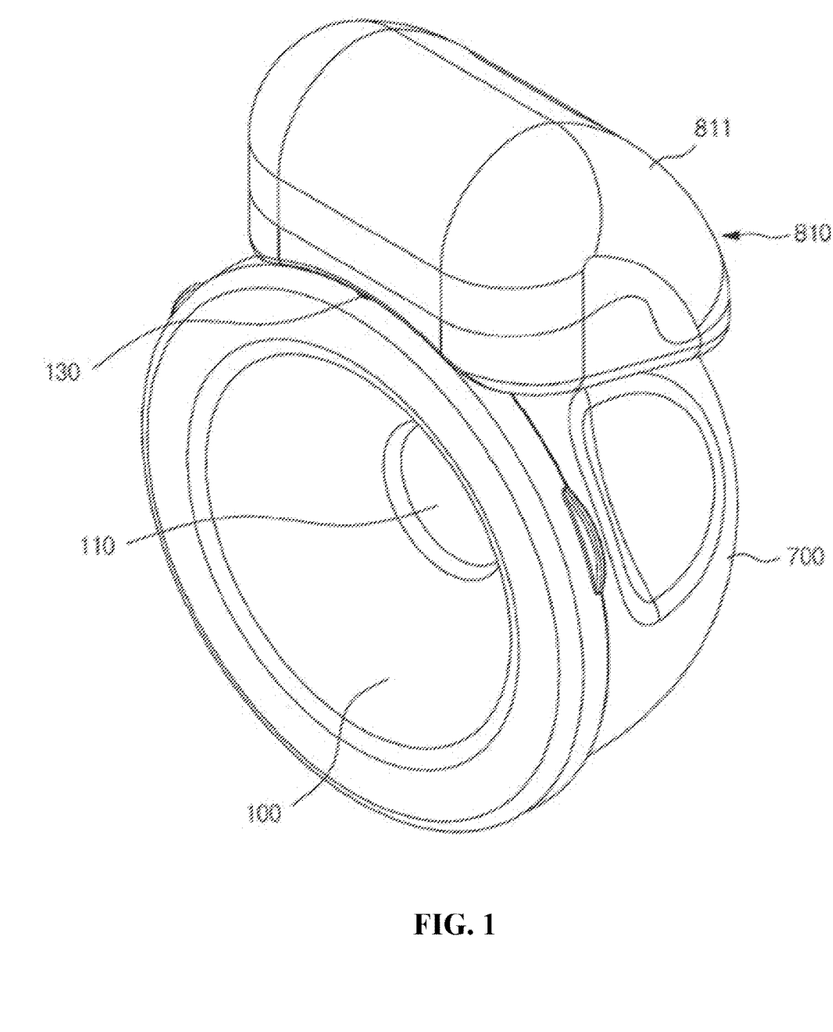
FIG. 1 is a perspective view illustrating a breast pump according to an embodiment of the present invention.
Figure 2:
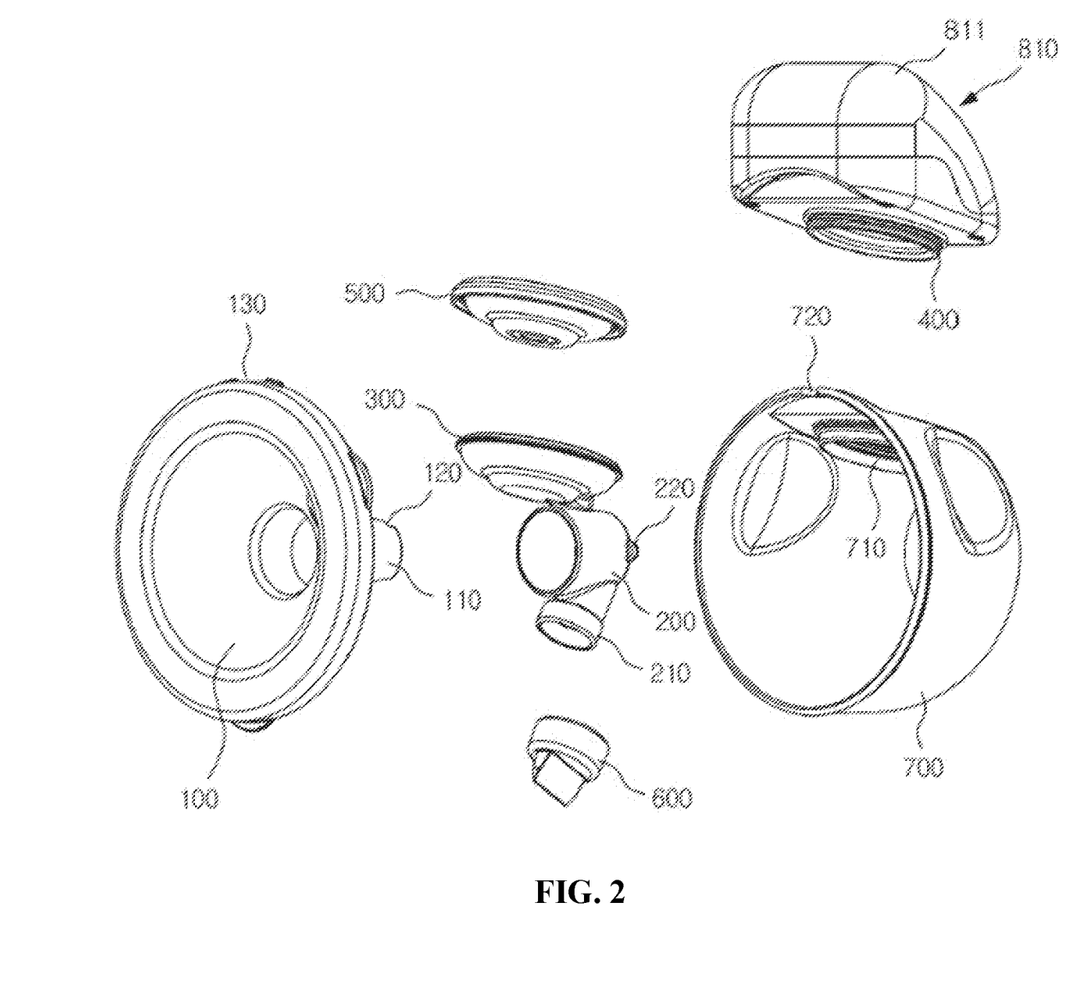
FIG. 2 and FIG. 3 are exploded perspective views illustrating a breast pump according to an embodiment of the present invention.
Figure 3:
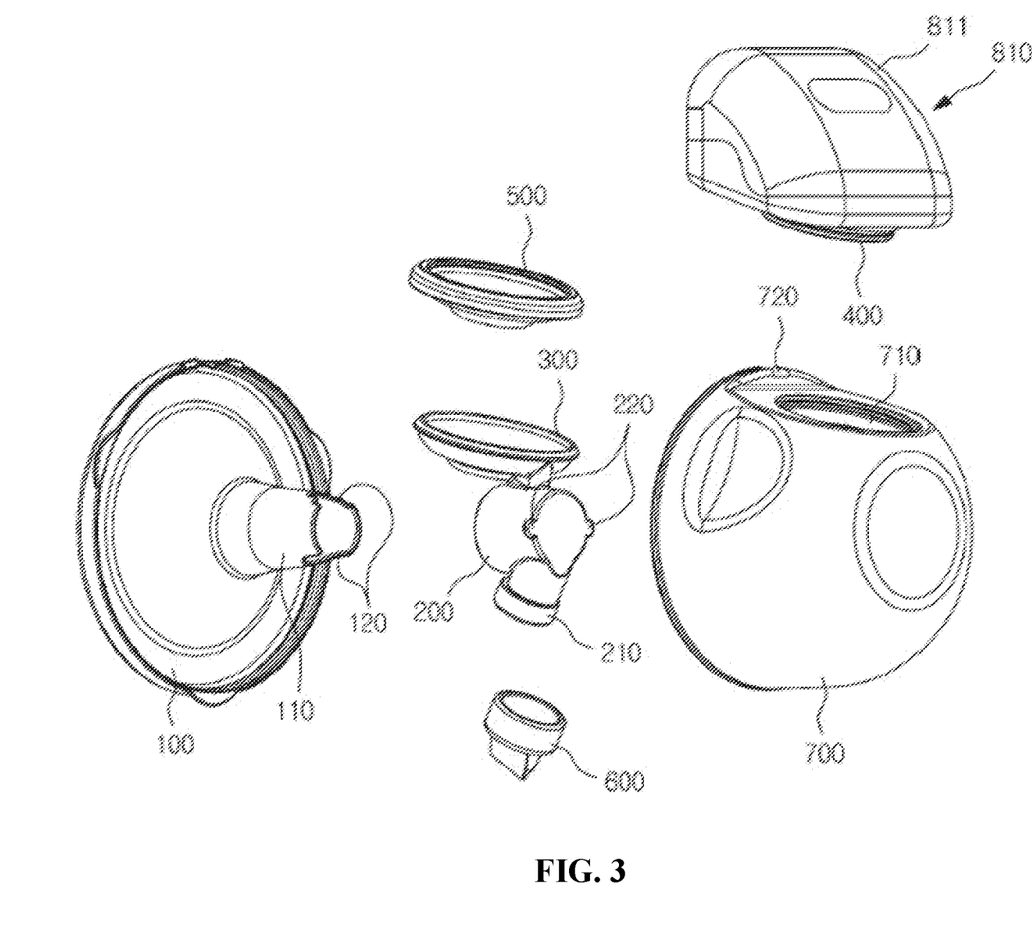

FIG. 1 is a perspective view illustrating a breast pump according to an embodiment of the present invention and FIG. 2 and FIG. 3 are exploded perspective views illustrating a breast pump according to an embodiment of the present invention.

Referring to FIG. 1 to FIG. 3, the breast pump according to an embodiment of the present invention may include a contact housing 100, a cap connector 200, a funnel connector 300, a storage housing 700, a lid 400, and a flow separation membrane 500.

The contact housing 100 may include a protruding part 110 formed at a portion corresponding to a mother's nipple and extending toward the front and a breast milk outlet 120 formed through an end of the protruding part 110. The breast milk collected in a second inner space of the protruding part 110 is discharged through the breast milk outlet 120 to a breast milk outlet tube 210 of the cap connector 200 to be described later. In the present embodiment, the breast milk outlet 120 may be formed at an upper, lower or front of an end of the protruding part 110.

The cap connector 200 may be coupled to cover an end of the protruding part 110 to form a first inner space G between the end of the protruding part 110 and itself, and include a breast milk outlet tube 210 linking with the breast milk outlet 120 and the first inner space G. The cap connector 200 may be spaced apart from the part corresponding to the end of the protruding part 110 by a certain distance, rather than being in close contact with the end of the protruding part 110. As a result, the first inner space G is provided between the end of the protruding part 110 and the cap connector 200. The breast milk outlet tube 210 may extend downward from a lower portion of the cap connector 200 to link with the breast milk outlet 120 and the first inner space G.

The funnel connector 300 may be installed on a top of the cap connector 200 to form a second inner space. The funnel connector 300 may be formed with a concave upper surface to form the second inner space. A linking pathway 310 may be provided between the funnel connector 300 and the cap connector 200 to link the second inner space of the funnel connector 300 and the first inner space of the cap connector 200. Accordingly, the second inner space of the funnel connector 300 may be linked to the first inner space of the cap connector 200 and the breast milk outlet tube 210 through the linking pathway 310 and further to the protruding part 110 of the contact housing 100.

The storage housing 700 may be provided with a coupling hole 710 in a portion corresponding to the second inner space of the funnel connector 300 and be detachably coupled to the contact housing 100. The storage housing 700 of the present embodiment may be in close contact with the contact housing 100 to form a space in which the breast milk discharged through the breast milk outlet tube 210 of the cap connector 200 is stored. Therefore, breast milk may be collected without using a separate bottle during the breast pumping process and thus, a user may perform breast pumping without requiring a separate bottle while freely using both hands.

In addition, since the storage housing 700 is detachably coupled to the contact housing 100, a user may detach the storage housing 700 from the contact housing 100 to store the milk in another place after a certain amount of breast milk is collected inside the storage housing 700.

The storage housing 700 may be further provided with a breast milk outlet hole 720 to transfer the milk in the storage housing 700 to the outside even if the storage housing 700 is not separated from the contact housing 100. For example, a first breast milk outlet hole 720 for discharging the stored breast milk to the outside may be provided at an upper portion of the storage housing 700 and a second breast milk outlet hole 130 linked with the first breast milk outlet hole 720 may be provided at an upper portion of the contact housing 100. Therefore, a user may not need to separate the storage housing 700 from the contact housing 100 to transfer the milk to another place through the first and the second breast milk outlet holes 720, 130 after a certain amount of breast milk is collected inside the storage housing 700. At this time, the first and the second breast milk outlet holes 720, 130 may be further provided with a stopper 430 for opening and closing.

Figure 4:
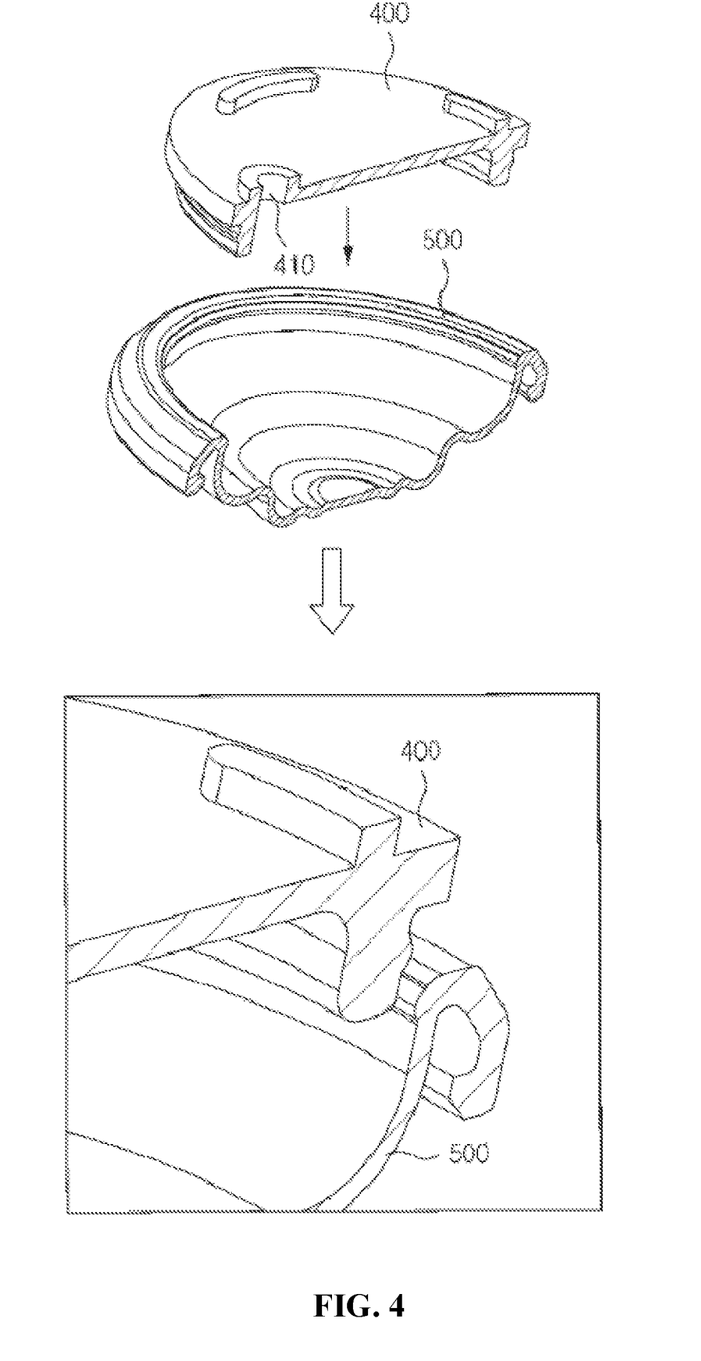
FIG. 4 is an exploded cross-sectional view illustrating a coupling between a lid and a flow separation membrane of a breast pump according to an embodiment of the present invention.

FIG. 4 is an exploded cross-sectional view illustrating a coupling between a lid and a flow separation membrane of a breast pump according to an embodiment of the present invention.

Referring to FIG. 4, the lid 400 of this embodiment may be coupled to cover the second inner space of the funnel connector 300 through the coupling hole 710 of the storage housing 700. The lid 400 may be provided with an air pathway 410 to penetrate vertically. The air pathway 410 may serve to flow air into and out from the space between the lid 400 and the flow separation membrane 500.

Figure 5:
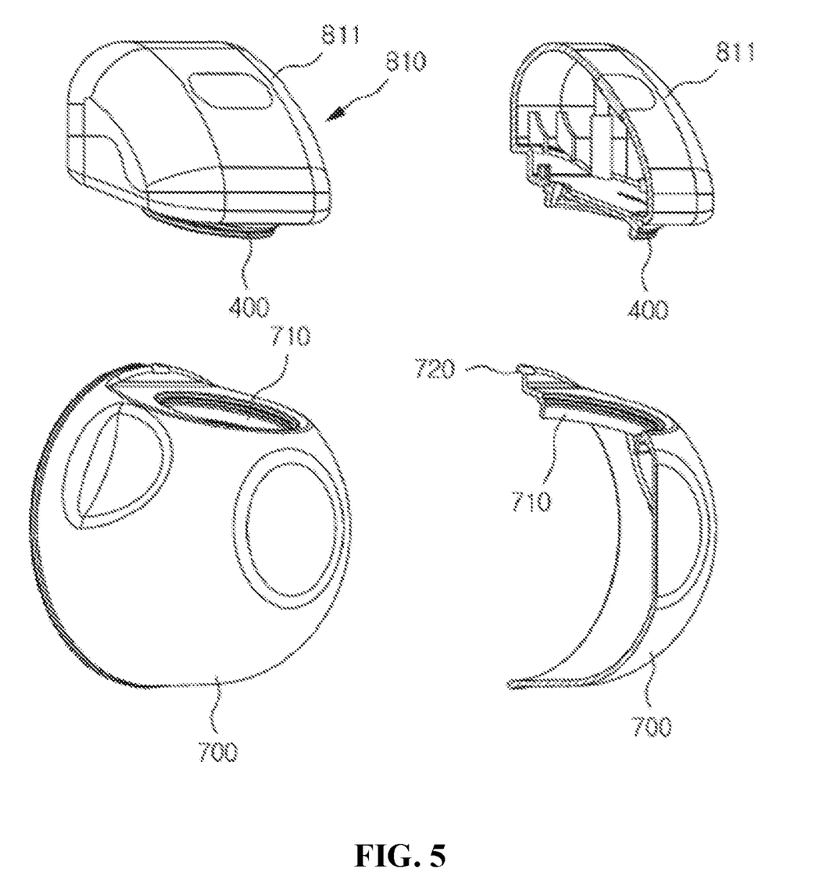
FIG. 5 is an exploded cross-sectional view illustrating a coupling between a storage housing and an attachable pump module of a breast pump according to an embodiment of the present invention.

FIG. 5 is an exploded cross-sectional view illustrating a coupling between a storage housing and an attachable pump module of a breast pump according to an embodiment of the present invention.

As shown in FIG. 5, the breast pump of this embodiment may further include an attachable pump module 810 on the lid 400 to suck the air between the lid 400 and the flow separation membrane 500 through the air pathway 410.

Unlike the conventional detached electric pump, the attachable pump module 810 may include an external case 811 and an electric pump (not shown) installed inside the external case 811, which are configured to be integrally attached to the storage housing 700. Referring to FIG. 5, the attachable pump module 810 may be integrally coupled with the lid 400 to be detachably coupled to the coupling hole 710 of the storage housing 700. Therefore, since the attachable pump module 810 is integrally attached to the storage housing 700 through the coupling hole 710 and the lid 400, compared to the conventional structure in which an electric pump and a lid are connected through an air pipe 420, a mother is able to freely move or use hands during the breast pumping while wearing the breast pump of this embodiment in the bra.

The flow separation membrane 500 is a member that divides and separates the space between the funnel connector 300 and the lid 400. The flow separation membrane 500 may be made of a material having ductility so that it can be easily bent by external force.

When the air between the lid 400 and the flow separation membrane 500 is sucked out through the air pathway 410 by the operation of the attachable pump module 810, the flow separation membrane 500 may move upward, thereby the space between the flow separation membrane 500 and the funnel connector 300 may be expanded to form a vacuum pressure, which is then transferred to the linking pathway 310, the first inner space, the breast milk outlet tube 210, and the second inner space of the protruding part 110 to act as a force for extracting breast milk from a mother's breast.

According to this embodiment, even if the mother's breast milk is sucked into the inner space of the funnel connector 300 through the first inner space and the linking pathway 310 by the vacuum pressure, the breast milk may not be flowed into the electric pump through the air pathway 410 since the inner space of the funnel connector 300 is vertically separated by the flow separation membrane 500. Since the breast milk does not flow out by the flow separation membrane 500, it is possible to solve problems such as contamination or damage of the electric pump by the breast milk.

The breast pump of the present embodiment may further include a silicone valve 600, one end of which is coupled to an outlet side of the breast milk outlet tube 210 and the other pointed end is provided with a cut line (not shown). The silicone valve 600 may prevent the breast milk filled in the storage housing 700 from flowing back into the cap connector 200 and the second inner space of the funnel connector 300 through the breast milk outlet tube 210. Therefore, the breast milk that is flowed out through the breast milk outlet tube 210 may be flowed into the silicon valve 600 and then be filled into the storage housing 700 through the cut line. However, since the breast milk in the storage housing 700 may not be flowed into the silicon valve 600 through the cut line, it is possible to prevent the breast milk in the storage housing 700 from flowing back to the mother's breast.

Figure 6:
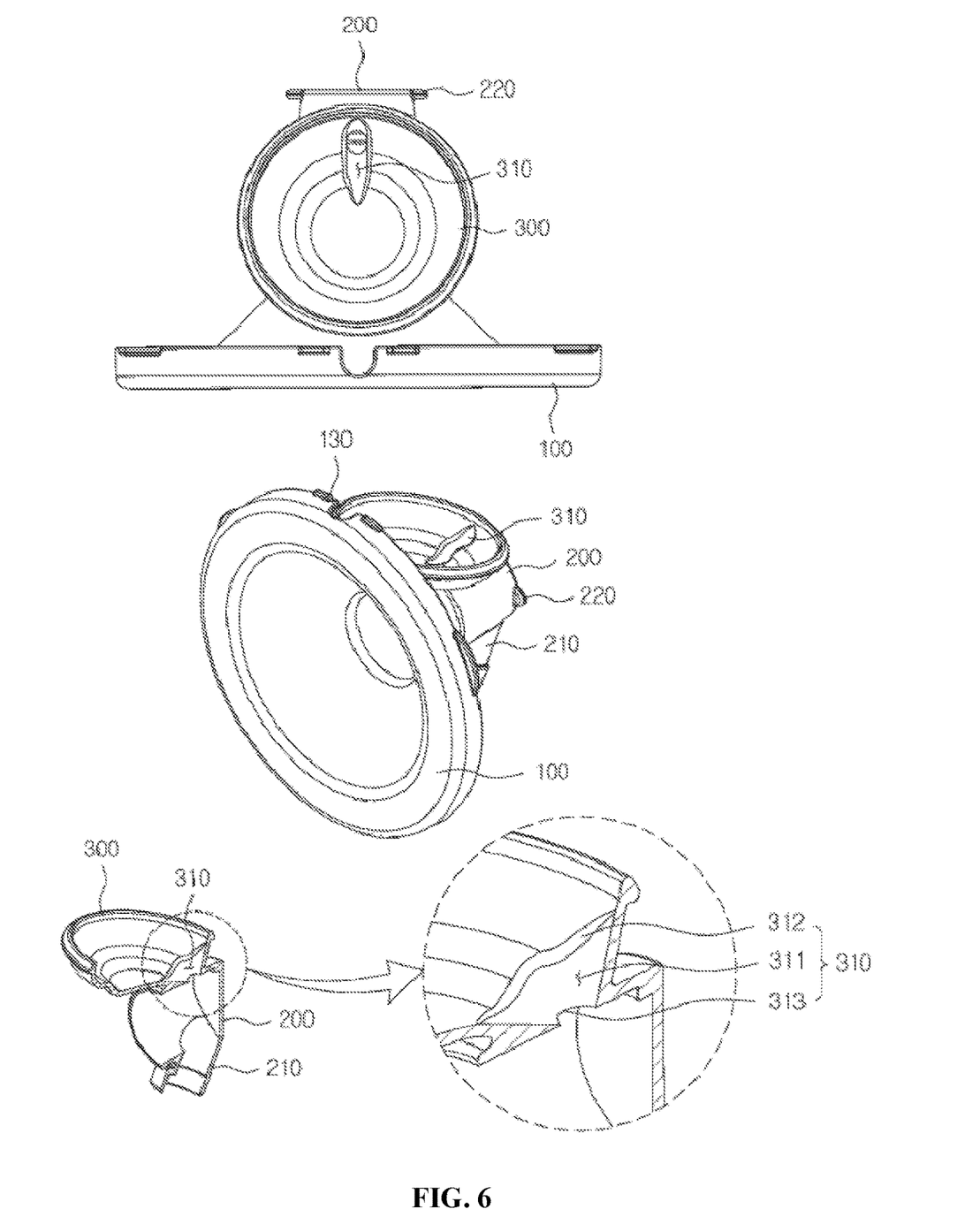
FIG. 6 is an exploded perspective view illustrating a cap connector and a funnel connector of a breast pump according to an embodiment of the present invention.

FIG. 6 is an exploded perspective view illustrating a cap connector and a funnel connector of a breast pump according to an embodiment of the present invention.

The breast milk in the protruding part 110 may be introduced to the linking pathway 310 by the vacuum pressure. If the linking pathway 310 is not exposed to the outside, it is difficult to clean the linking pathway 310, thereby causing contamination and bacterial propagation. Therefore, it is needed to facilitate cleaning and maintenance of the linking pathway 310.

Referring to FIG. 6, the linking pathway 310 of the present embodiment may include a space part 311 in an inverted triangle (V) shape, a first cleaning hole 312 in an elongated shape linking with the second inner space of the funnel connector 300 around the space part 311, and a second cleaning hole 313 located opposite the first cleaning hole 312 and linking with the first inner space of the cap connector 200. A longitudinal length of the first cleaning hole 312 may be longer than a longitudinal length of the second cleaning hole 313. In addition, the longitudinal length of the first cleaning hole 312 may be longer than a depth in a vertical direction of the space part 311. Therefore, as the linking pathway 310 between the cap connector 200 and the funnel connector 300 is configured to be the shortest distance, it may be facilitate cleaning milk, foreign substances, or the like stuck in the linking pathway 310 and maintenance.

Figure 7:
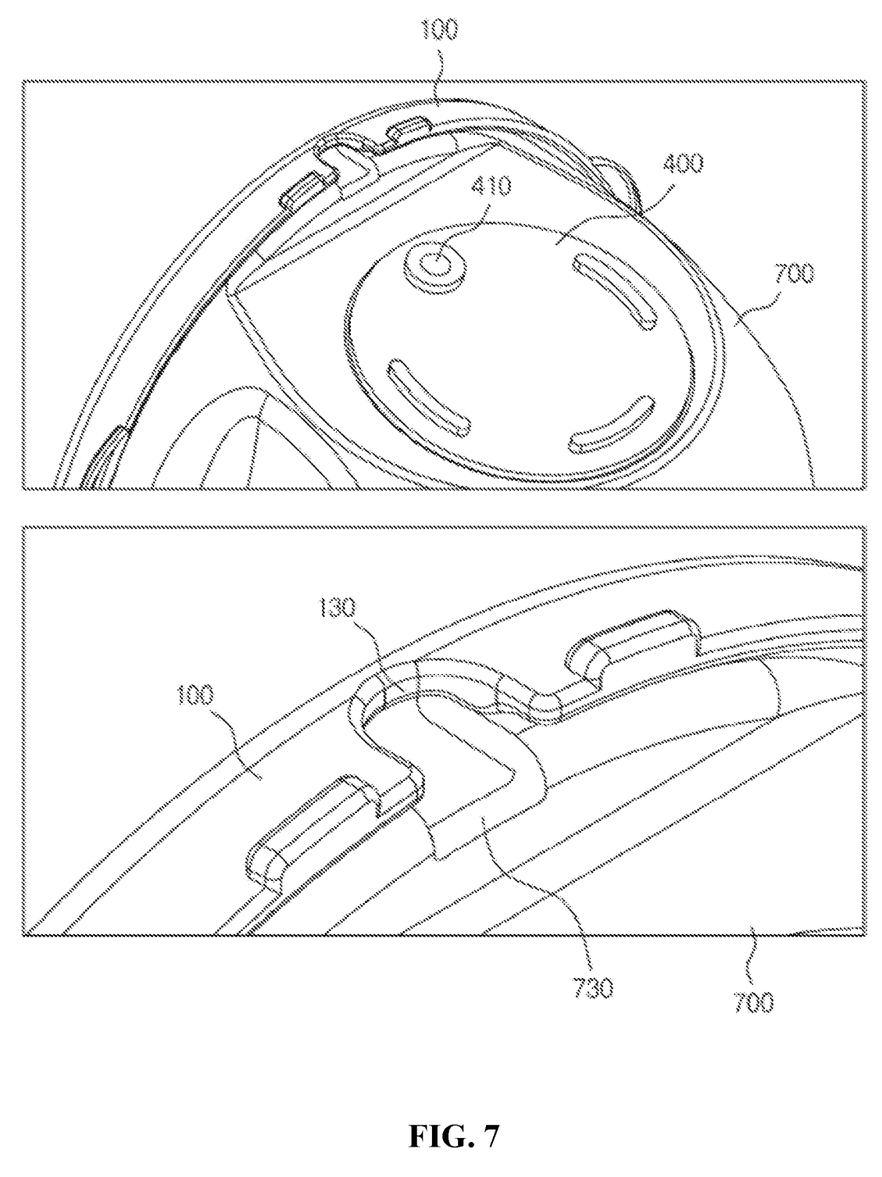
FIG. 7 is a perspective view illustrating a coupling between a storage housing and a contact housing of a breast pump according to an embodiment of the present invention.

FIG. 7 is a perspective view illustrating a coupling between a storage housing and a contact housing of a breast pump according to an embodiment of the present invention.

The contact housing 100 and the storage housing 700 may be combined, for example, in an interference fit. For example, a concave groove and a convex step corresponding thereto may be provided at portions where the contact housing 100 and the storage housing 700 come into contact with each other to increase the coupling. Therefore, the concave groove and the convex step are engaged with each other to increase the coupling force when coupled by the interference fit. The breast bump may further include a sealing member (not shown) that closes the gap between the contact housing 100 and the storage housing 700. The sealing member may be made of a ring shape of an elastic material such as rubber.

Similarly, a concave groove may be formed on an inner surface of the coupling hole 710 and a convex step corresponding to the concave groove may be formed on a lower surface of the lid 400 to increase the coupling force between the lid 400 and the coupling hole 710 as shown in FIG. 5.

The lid 400 may be made of a material having strength sufficient to withstand the shape without deformation against the vacuum pressure when the vacuum pressure is generated. The lid 400 may be coupled to a lower surface of the external case 811 of the attachable pump module 810, wherein a plurality of coupling protruding parts are provided on an upper surface of the lid 400 and coupling grooves corresponding to the coupling protruding parts are provided on a lower surface of the external case 811. Thus, the external case 811 maybe coupled through the coupling protruding parts and the coupling grooves in addition to the lid 400.

The contact housing 100 and the storage housing 700 may be provided with an identification mark on the joint portion to keep a constant coupling angle between them. The cross section may be formed in a non-circular shape for a user to grip firmly and turn the contact housing 100 and the storage housing 700. The shapes of the contact housing 100 and the storage housing 700 may be formed in various shapes without any limitation.

A seating groove may be further provided at an end of the protruding part 110 so that one side does not rotate relative to the other side when the protruding part 110 of the contact housing 100 and the cap connector 200 are coupled, and a seating protrusion may be further provided at an inner side of the cap connector 200 to be fitted in the seating groove by a shrink fit manner. It thus prevents the cap connector 200 from being loose with respect to the protruding part 110.

Figure 8:
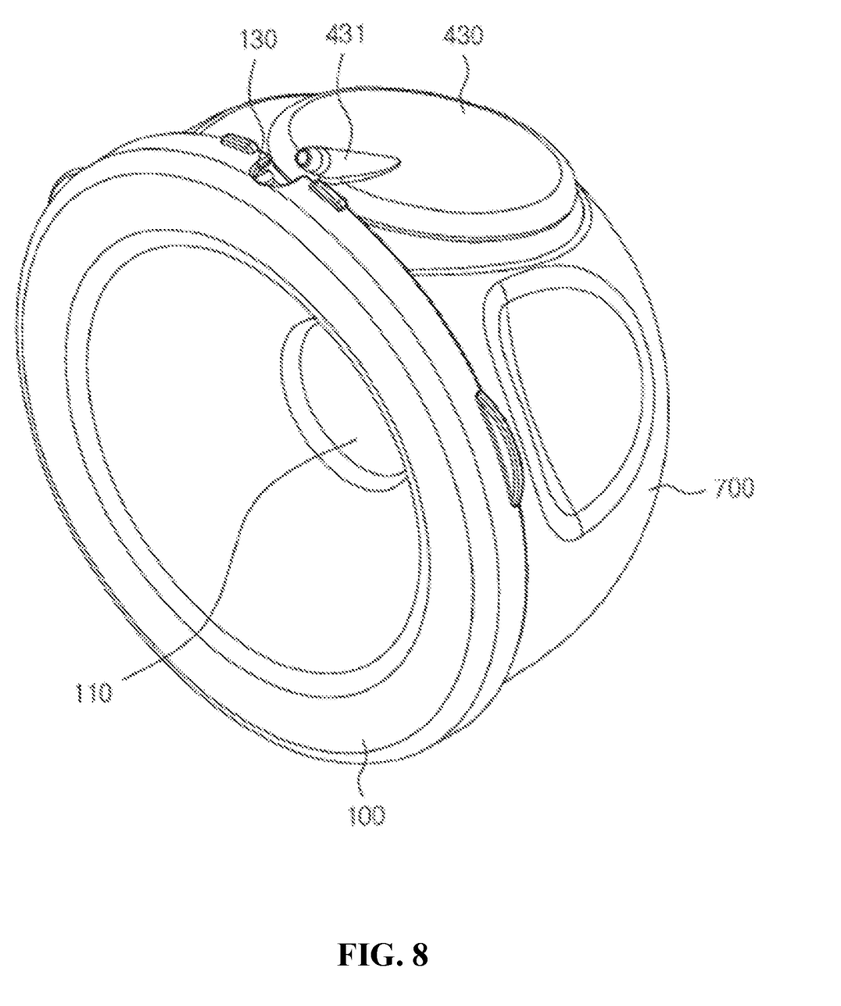
FIG. 8 is a perspective view illustrating a modified example of a breast pump according to an embodiment of the present invention.
Figure 9:
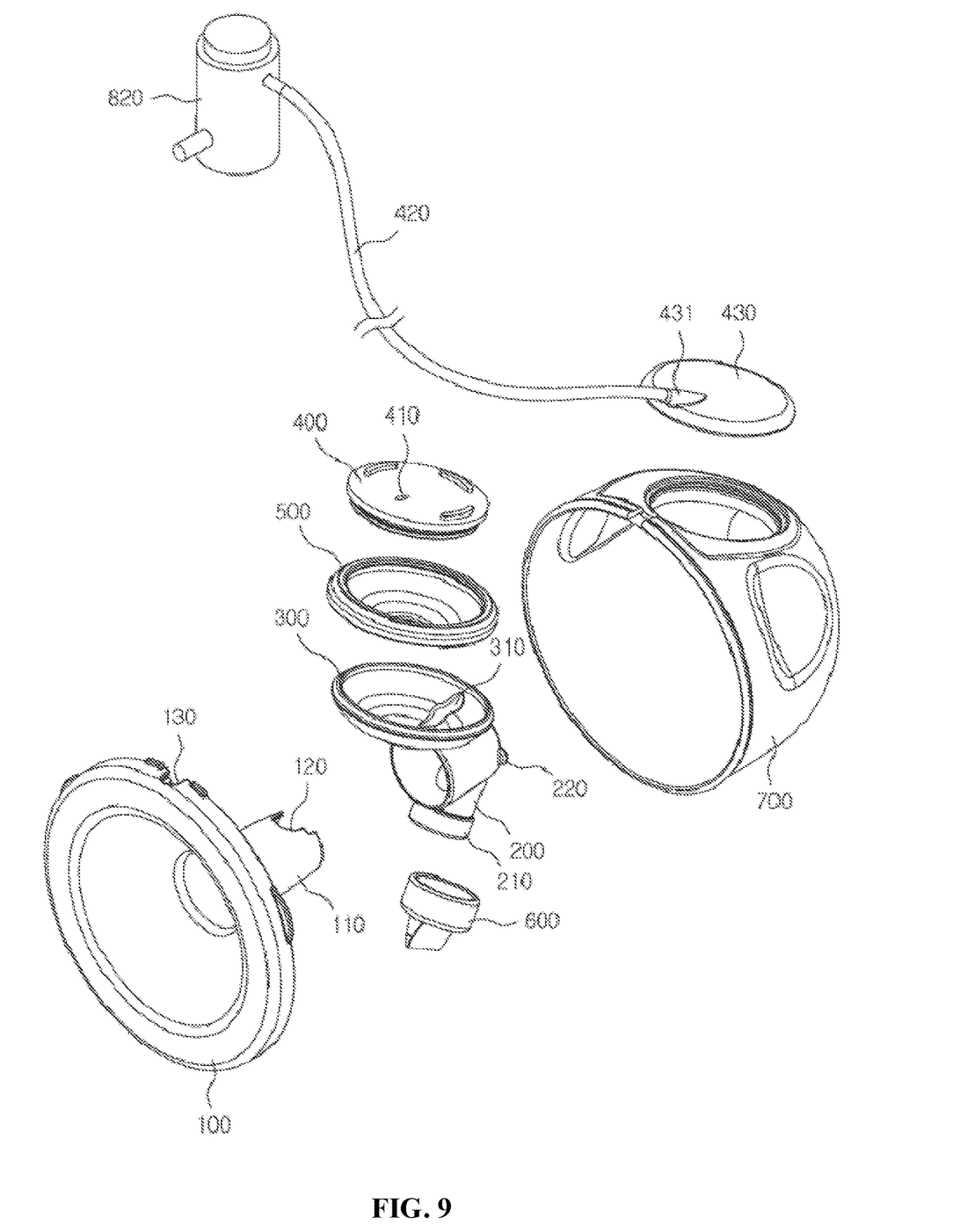
FIG. 9 is an exploded perspective view illustrating another modified example of a breast pump according to an embodiment of the present invention.

FIG. 8 is a perspective view illustrating a modified example of a breast pump according to an embodiment of the present invention and FIG. 9 is an exploded perspective view illustrating another modified example of a breast pump according to an embodiment of the present invention.

The breast pump according to the present embodiment may further include an external electric pump 820 instead of the attachable pump module 810 and an air pipe 420 connecting between the lid 400 and the external electric pump 820. The external electric pump 820 may be configured to operate separately from the breast pump body in a different form from the attachable pump module 810 which is integrally attached to the breast pump body. The external electric pump 820 may be connected to the lid 400 coupled to the coupling hole 710 of the storage housing 700 through the air tube 420 to enable air flow.

In this case, a stopper 430 having an air pipe connector 431 linked with the air pathway 410 of the lid 400 may be additionally provided on the lid 400. The air pipe connector 431 may be detachably connected to the air pipe 420 for intake of air. Therefore, the air between the lid 400 and the flow separation membrane 500 may be sucked through the air pipe 420 by operating the external electric pump 820 to generate vacuum pressure.

The configuration of the breast pump according to an embodiment of the present invention has been described above. Hereinafter, a configuration of a breast pump according to another embodiment of the present invention will be described. In the description of the breast pump according to another embodiment of the present invention, a description of a configuration overlapping with the configuration of the breast pump described above will be omitted for convenience of description.

Figure 10:
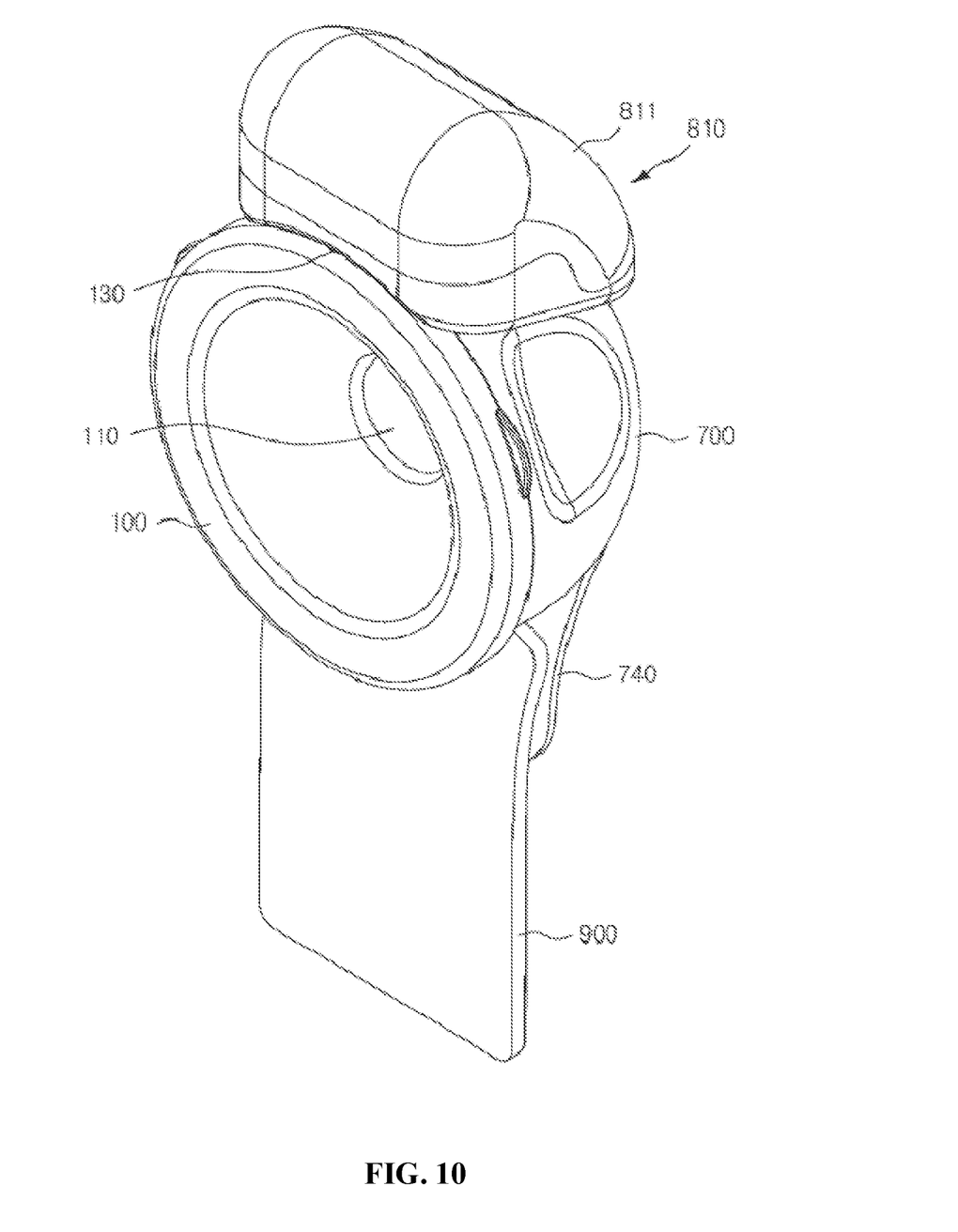
FIG. 10 is a perspective view illustrating a breast pump according to another embodiment of the present invention.
Figure 11:
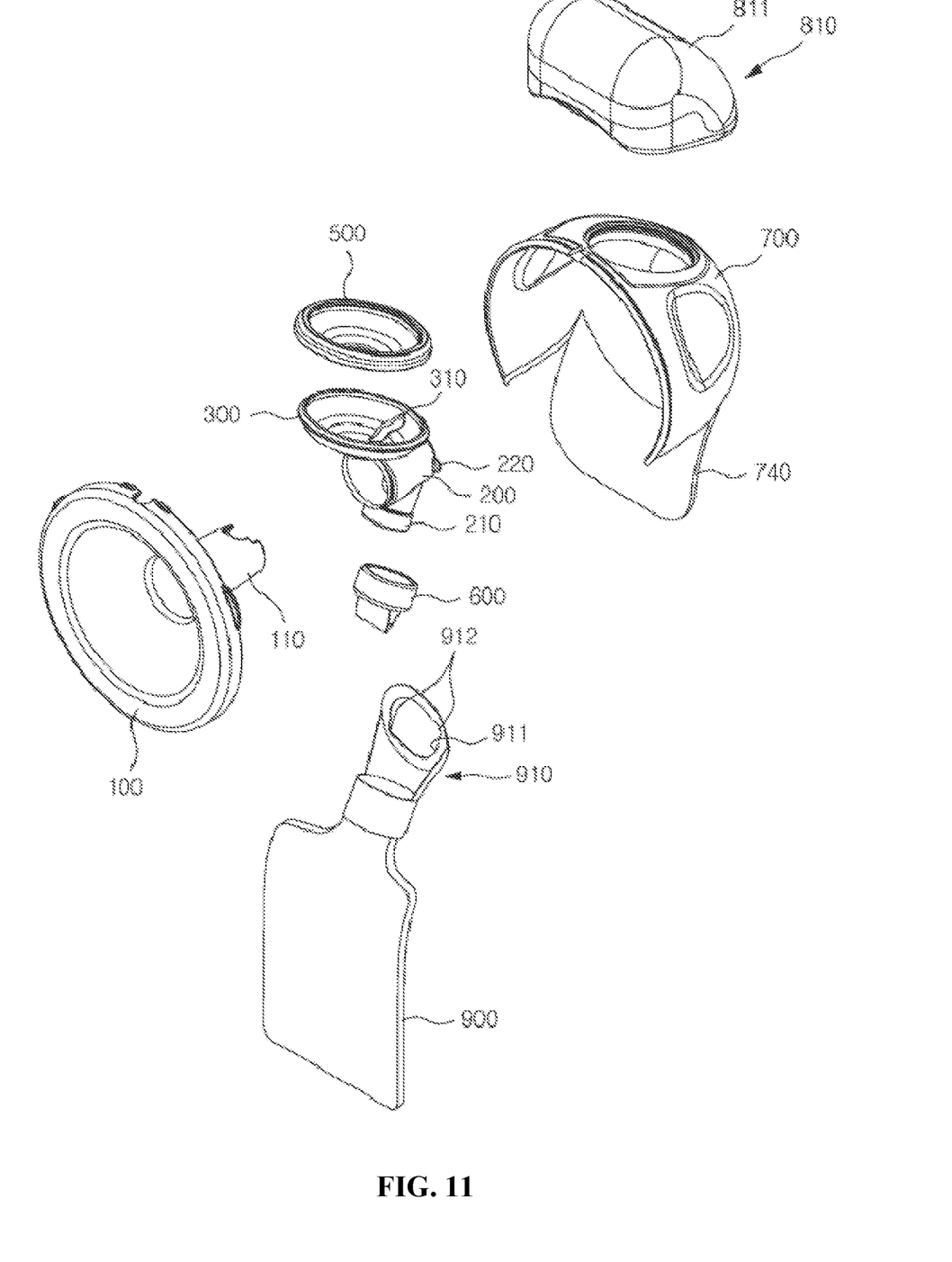
FIG. 11 is a perspective view illustrating a breast pump according to further another embodiment of the present invention.

FIG. 10 is a perspective view illustrating a breast pump according to another embodiment of the present invention and FIG. 11 is a perspective view illustrating a breast pump according to further another embodiment of the present invention.

A zipper bag insertion hole 730 may be formed at a lower portion of the storage housing 700. The zipper bag insertion hole 730 may have a structure that allows a breast milk zipper bag 900 to be inserted into the storage housing 700 as shown in FIG. 10 and FIG. 11.

The breast pump may be inserted into the inside of the bra, which a nursing mother wears, to operate the pump. The breast pump may further include an anti-pressing plate 740 formed to extend a surface of the storage housing 700 downward from the zipper bag insertion hole 730 in order to prevent the bra from squeezing a breastmilk zipper bag 900. The anti-pressing plate 740 may have a structure in which the surface of the storage housing 700 is further extended downwardly from a portion in contact with the zipper bag insertion hole 730 as shown in the drawing. Therefore, the breast milk may be extracted and collected to the breastmilk zipper bag 900 without squeezing the breastmilk zipper bag 900 by the bra while a nursing mother keeps her bra on.

A zipper bag fixation hook 220 may be additionally provided at an end of the cap connector 200 so as to fix the breast milk zipper bag 900 inside the storage housing 700. The zipper bag fixation hook 220 may be, for example, a semi-circular protrusion structure. However, the shape of the zipper bag fixation hook 220 is not limited thereto. The semi-circular zipper bag fixation hook 220 may be provided as a pair at an end of the cap connector 200 at an interval of 180 degrees. The zipper bag fixation hook 220 may be coupled with the breast milk zipper bag 900 having a locking part 910 to be described later.

The breast pump of this embodiment may further include a breastmilk zipper bag 900 having a locking part 910 formed to be hooked to the zipper bag fixation hook 220. Unlike the conventional breastmilk zipper bag 900, the breastmilk zipper bag 900 of this embodiment may have a structure in which an upper end of the breastmilk zipper bag 900 is extended upwardly and the extended portion is detachably coupled to the zipper bag fixation hook 220 as the locking part 910.

Referring to FIG. 11, the locking part may include a first locking hole 911 formed to be hooked to an end of the cap connector and a second locking hole 912 formed on an inner periphery or an inner peripheral surface of the first locking hole 911. A shape of the first locking hole 911 may correspond to that of an end of the cap connector and a shape of the second locking hole 912 may correspond to that of the zipper bag fixation hook 220.

According to the embodiments of the present invention as described above, there are various advantages such as that a nursing mother can freely move or enjoy other activities during the operation of the breast pump since it can be worn and carried within the bra, its cleaning and maintenance after use can be easier since the linking pathway 310 between the cap connector 200 and the funnel connector 300 becomes the shortest distance, it is possible to prevent breast milk from flowing back through the flow path to which vacuum pressure is applied, it is configured to be compatible with an existing electric pump by separating the attachable pump module 810 if needed, and the breast milk can be extracted and collected to the breastmilk zipper bag 900 without squeezing the breastmilk zipper bag 900 by the bra while a nursing mother keeps her bra on.

Although a certain embodiment of the present invention has been described above, it shall be appreciated that there can be a variety of permutations and modifications of the present invention by those who are ordinarily skilled in the art to which the present invention pertains without departing from the technical ideas and scope of the present invention, which shall be defined by the appended claims. It shall be also appreciated that many embodiments other than the embodiment described above are present in the claims of the present invention.

What is claimed is:

1. A breast pump comprising:
    a contact housing comprising a protruding part configured to correspond to a mother's nipple and extend toward a front of the breast pump and a breast milk outlet formed at the protruding part;
    a cap connector coupled to cover an end of the protruding part to form a first inner space between the end of the protruding part and the cap connector, and further comprising a breast milk outlet tube linked with the breast milk outlet and the first inner space;
    a funnel connector on the cap connector to form a second inner space;
    a storage housing comprising a coupling hole to correspond to the second inner space of the funnel connector, the storage housing detachably coupled with the contact housing;
    a lid coupled to cover the second inner space of the funnel connector through the coupling hole of the storage housing; and
    a flow separation membrane configured to divide and separate the second inner space between the funnel connector and the lid into a first portion and a second portion,
    wherein a linking pathway is provided between the funnel connector and the cap connector to link the first portion of the second inner space of the funnel connector with the first inner space of the cap connector,
    wherein the linking pathway comprises:
    a space part in an inverted triangle (∇) shape;
    a first cleaning hole in an elongated shape linking the space part with the second inner space of the funnel connector; and
    a second cleaning hole located opposite the first cleaning hole and linking the space part with the first inner space of the cap connector.

2. The breast pump of claim 1, further comprising an air pathway in the lid through which air flows into and out from the second portion of the second inner space between the lid and the flow separation membrane, and an attachable pump module on the lid to suck the air between the lid and the flow separation membrane through the air pathway.

3. The breast pump of claim 1, further comprising:
    an air pathway in the lid through which air flows into and out from the second portion of the second inner space between the lid and the flow separation membrane;
    a stopper on the lid having an air pipe connector linked with the air pathway;

an air pipe detachably connected to the air pipe connector; and an external electric pump configured to suck the air between the lid and the flow separation membrane through the air pipe.

4. The breast pump of claim 1, further comprising a silicone valve comprising one end coupled to an outlet of the breast milk outlet tube and a second pointed end comprising a cut line.

5. The breast pump of claim 1, further comprising a zipper bag insertion hole formed through a lower portion of the storage housing; and a zipper bag fixation hook provided in the cap connector.

6. The breast pump of claim 5, further comprising an anti-pressing plate formed to extend a surface of the storage housing downward from the zipper bag insertion hole to prevent a bra from compressing a breastmilk zipper bag.

7. The breast pump of claim 5, further comprising a breastmilk zipper bag having a locking part to be hooked to the zipper bag fixation hook, wherein the locking part comprises a first locking hole to be hooked to an end of the cap connector and a second locking hole formed on an inner periphery or inner peripheral surface of the first locking hole, wherein a shape of the first locking hole corresponds to a shape of the end of the cap connector, and wherein a shape of the second locking hole corresponds to a shape of the zipper bag fixation hook.

\* \* \* \* \*